United States Patent

Burns, Sr. et al.

Patent Number: 5,374,253
Date of Patent: Dec. 20, 1994

[54] MEDICAL INSTRUMENT WITH AUTOMATIC SHUT-OFF VALVE

[76] Inventors: Charles N. Burns, Sr., 455 Wyoming Ave., Kingston, Pa. 18702; James J. Lennox, 90 Oak St., Forty Fort, Pa. 18704; Clifford R. Mirman, 151 Catalpa Ave., Mountain Top, Pa. 18707

[21] Appl. No.: 133,836
[22] Filed: Oct. 12, 1993
[51] Int. Cl.$^5$ ............................................. A61M 5/00
[52] U.S. Cl. ........................................ 604/169; 604/33
[58] Field of Search ........................................ 128/4-8; 604/33, 167, 169, 249, 283

[56] References Cited

U.S. PATENT DOCUMENTS

| | | |
|---|---|---|
| 3,149,633 | 9/1964 | Zingale . |
| 3,791,379 | 2/1974 | Storz . |
| 3,850,162 | 11/1974 | Iglesias . |
| 4,060,086 | 11/1977 | Storz . |
| 4,068,667 | 1/1978 | Iglesias . |
| 4,657,018 | 4/1987 | Hakky . |
| 4,745,950 | 5/1988 | Mathieu . |
| 5,006,114 | 4/1991 | Rogers et al. . |
| 5,125,910 | 6/1992 | Freitas . |
| 5,156,142 | 10/1992 | Anapliotis et al. . |
| 5,195,958 | 5/1983 | Phillips . |
| 5,209,219 | 5/1993 | Hollobaugh ............................ 128/4 |
| 5,248,298 | 9/1993 | Bedi et al. . |

Primary Examiner—Richard J. Apley
Assistant Examiner—John Mulcahy
Attorney, Agent, or Firm—Nies, Kurz, Bergert & Tamburro

[57] ABSTRACT

A medical instrument such as an endoscopic or laparoscopic instrument comprising a tubular sheath assembly through which a variety of surgical tools may be axially inserted to perform desired medical procedures. The sheath assembly includes a cylindrical barrel having an irrigation fluid passageway and valve means associated with the passageway for automatically opening and closing the passageway in response to the insertion and removal of a tool from the sheath.

17 Claims, 2 Drawing Sheets

MEDICAL INSTRUMENT WITH AUTOMATIC SHUT-OFF VALVE

This invention relates generally to medical instruments such as endoscopic and laparoscopic instruments which include a tubular sheath insertable into a part of the human body and more particularly to such instruments in which the tubular sheath may selectively receive a number of operative surgical tools such as a telescope or other camera tool, a cutting tool, a forceps tool, etc. Although the invention has general application to various types of medical instruments, it will be described with respect to endoscopic instruments which are widely used in urology and are introduced through the urethra into the bladder for the purpose of conducting certain medical examinations and procedures by way of instruments such as a resectoscope, urethro-cystoscope, lithotriptor and biopsy endoscopic forceps.

All of those instruments include an elongated tubular sheath which is introduced through the urethra into the bladder. The sheath provides a tubular passageway through which various medical devices, such as a camera tool, a cutting tool, a biopsy forceps tool, etc., may be inserted to perform certain procedures within the bladder or on the prostate as may be necessary. The tubular sheath is conventionally provided with a supply line by which irrigation fluid, such as water, is introduced into the bladder during the particular medical procedure. In conventional prior art instruments, the supply line is usually provided with a manual valve which must be operated by the urologist to control the amount of fluid introduced into the sheath and to shut off the valve when the urologist is removing one medical tool from the sheath and replacing it with another. During this replacement step, it is not unusual for the urologist to leave the supply valve open, causing the irrigation fluid to flow continuously and spill from the tubular sheath, thus wasting a great deal of fluid and creating a mess around the patient. Typical prior art endoscopic instruments are illustrated in U.S. Pat. Nos. 3,149,633, 3,850,162, 4,060,086 and 4,068,667.

SUMMARY OF THE INVENTION

Accordingly, it is a primary object of this invention to provide a medical instrument such as an endoscope in which the tubular sheath includes a valve which is automatically opened and closed as a medical tool is inserted into and removed from the tubular sheath, thereby providing irrigation fluid to the sheath when the tool is in operative position, but blocking the flow of fluid when the tool is removed from the sheath.

Another object of the invention resides on the provision of the above novel medical instrument in which the tubular sheath includes a barrel and the valve is mounted within the barrel for axial sliding movement between closed and opened positions as a tool is inserted into and removed from the sheath.

A further object of the invention resides in the provision of the above-described medical instrument in which the barrel includes a fluid inlet opening in its side wall and in which the valve is a cylindrical piston axially slidably mounted within the barrel between a first position in which it blocks said opening and a second position in which it permits fluid flow through said opening into said barrel, the piston being actuated by a tool which is axially inserted into and removed from the sheath.

These and other objects of the invention will become more readily apparent from reading the following detailed description of the invention in which reference is made to the accompanying drawings wherein like numerals indicate like elements.

DETAILED DESCRIPTION OF THE INVENTION

Figure 1:
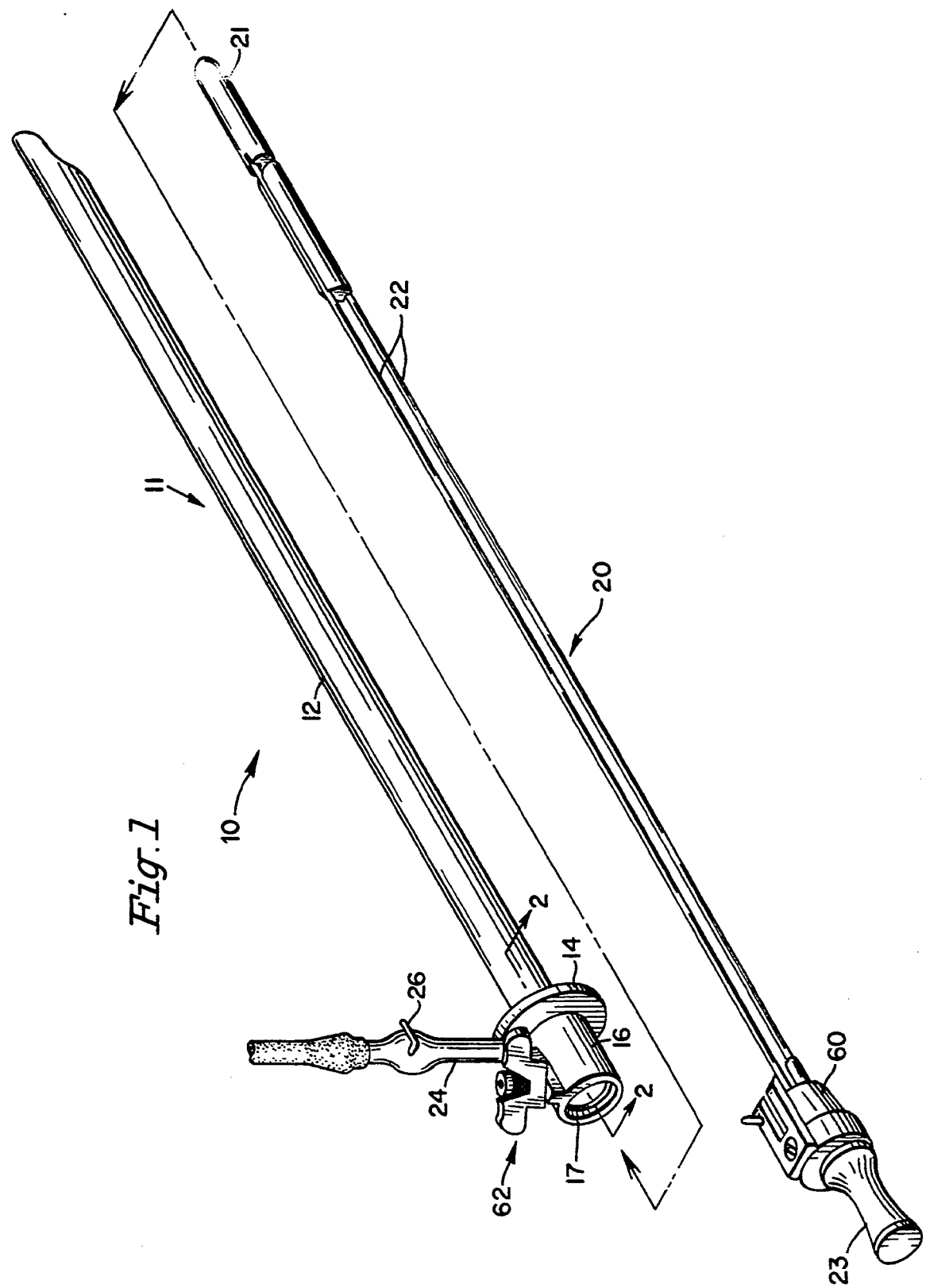
FIG. 1 is a general perspective view of the novel medical instrument of the invention illustrating the tubular sheath and a conventional medical tool removed from the sheath.

Referring to FIG. 1, the novel medical instrument 10 of the invention includes a sheath assembly 11 formed by a tubular glass fiber sheath 12 press-fitted within and through an annular flange or cap 14 to which is attached an external cylindrical barrel 16 open at its rear end 17. In an endoscopic instrument, the sheath 12 is capable of receiving a number of different medical tools such as conventional Timberlake guide tool 20 having a pivotable nose piece 21 actuated by pulling on rods 22 and handle 23. This guide tool assists the urologist in introducing the sheath 12 through the urethra over the prostate and into the bladder as required. Once the sheath 12 is in place, the guide tool 20 may be axially removed, and other conventional surgical tools, such as a cutting tool, a camera tool, a biopsy forceps tool, etc., may be axially inserted through the sheath to perform a desired medical procedure.

As in the prior art sheath assemblies, a fluid inlet conduit 24 is connected to a radial opening 25 in the sidewall of barrel 16 for introducing irrigation fluid through the barrel and sheath into the surgical area of the body to flush away resected tissue, blood, etc., and to keep the surgical tools clean. As in conventional instruments, a manually operated valve 26 may be mounted in line 24 and may be adjusted by the surgeon to control the amount of fluid flow through line 24.

As mentioned initially hereinabove, during an operation, it is not always necessary to have irrigation fluid flowing through sheath 12, and this is particularly true when the surgeon is changing from one surgical tool 20 to another. In a conventional instrument, it is necessary that the surgeon manually close a valve such as valve 26. Because the surgeon is trying to work very rapidly, quite often the valve is left open and the fluid continues to flow, thereby wasting a great deal of fluid and creating a mess and discomfort for the patient and attending medical personnel as the fluid exits out from the open end 17 of barrel 16.

To overcome this problem, the invention provides a novel valve assembly 30 within barrel 16 to automatically open and close the flow of fluid from line 24 to sheath 12 as a tool 20 is axially inserted into and removed from the sheath.

Cylindrical barrel 16 has a slightly tapered end bore 32 and an elongated axially-extending counter bore 34 defined at its outer end by a perpendicular shoulder 36 and at its other end by the perpendicular end face 38 of cap 14. A cylindrical valve piston 40, having an internal bore 42 sized to slidably fit over the outside diameter of the inner end 13 of sheath 12, has a rear turned section 44 sized to slide axially within counter-bore 34. Piston 40 also has a reduced forward turned section 46 on which a pair of axially spaced O-rings 48 and 50 are mounted. A coil spring 52 surrounds inner end 13 of sheath 12 and acts between the end face 38 of cap 14 and the front end face 54 of piston 40 to normally bias piston 40 to a rearward position in which end face 45 abuts against shoulder 36 and in which the O-rings 48 and 50 block the flow of fluid from line 24 to sheath 12 (FIG. 2).

Piston 40 is provided with an annular groove 56 adjacent its rear end and a plurality of drilled radial openings 58 by which groove 56 communicates with axial bore 42.

Figure 4:
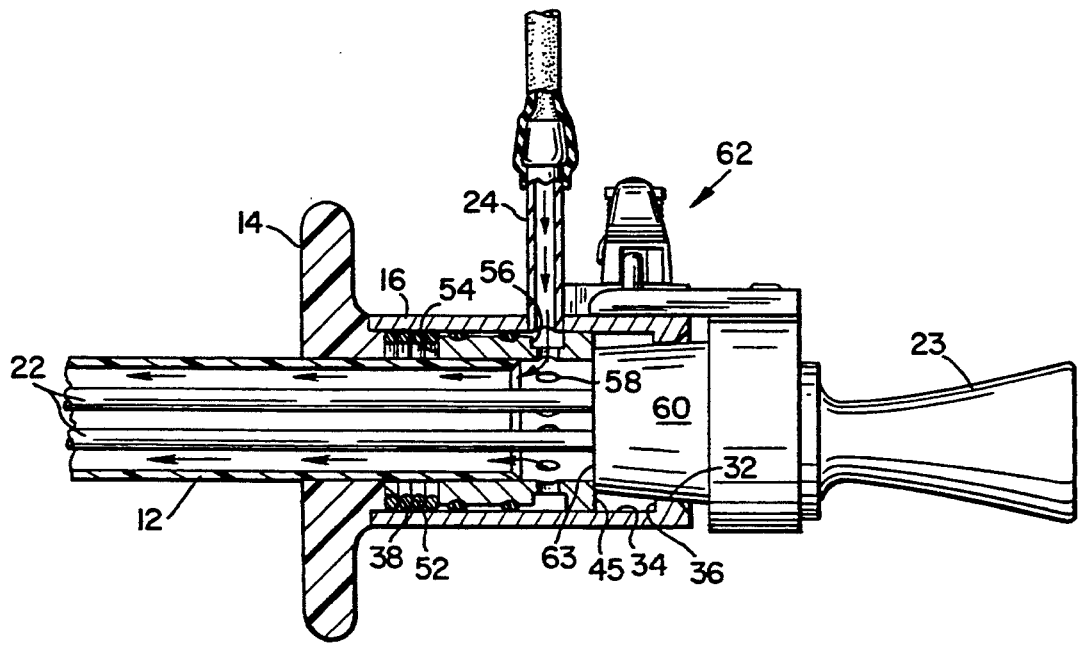
FIG. 4 is a view similar to FIG. 2 but with a conventional medical tool inserted into the sheath and actuating the valve to its open position.

Each of the conventional surgical tools 20 has a tapered plug section 60 which seats within the tapered bore 32 when the tool is fully inserted into sheath 12 as shown in FIG. 4 and in conventional fashion, this provides a fluid seal at the outer end 17 of barrel 16. A conventional spring-loaded keeper and lock mechanism 62, having cooperating parts on barrel 16 and tool 20, holds the tool in place as shown in FIG. 4.

Figure 2:
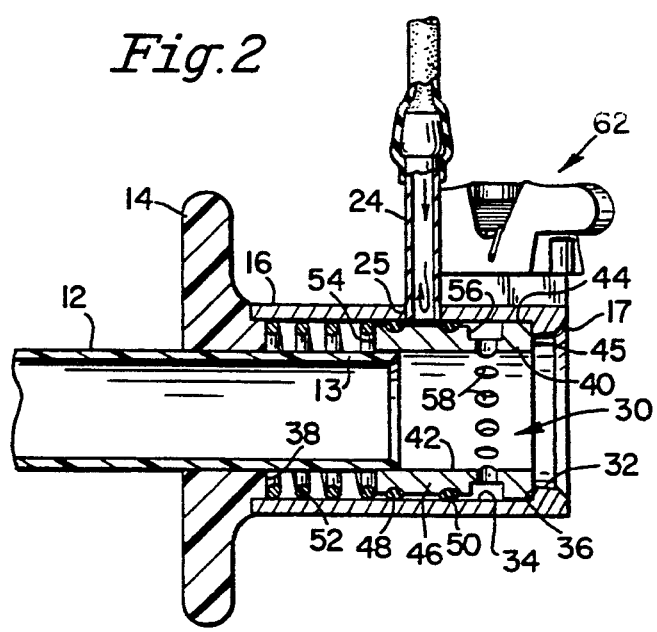
FIG. 2 is a fragmentary sectional view taken along line 2—2 of FIG. 1 and illustrating the barrel of the tubular sheath and the automatic shut-off valve mounted within the barrel in its closed position.
Figure 3:
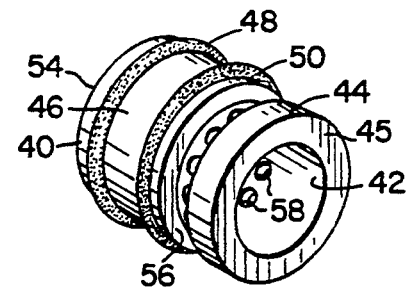
FIG. 3 is a perspective view of the cylindrical valve piston.

As shown in FIG. 2, with no tool inserted in sheath 12, piston 40 is retained by spring 52 into its rearward, closed position in which it blocks any fluid flow from line 24 into sheath 12. However, as shown in FIG. 4, when a tool 20 is inserted into the sheath, the end face 63 of plug 60 engages against rear end face 45 of piston 40 to push the piston axially forwardly to an open position in which annular groove 56 radially aligns with fluid line 24 to permit the flow of fluid through groove 56, openings 58 and bore 42, into the axial bore of sheath 12. Tapered plug 60 sealingly seats within bore 32 so that the fluid from line 24 is delivered to the surgical area of the patient through sheath 12.

It is readily apparent that, when the surgeon wishes to remove a tool 20 from sheath 12, as the tool is moved axially outwardly from barrel 16, spring 52 automatically biases piston 40 rearwardly to its closed position of FIG. 2, thereby automatically blocking the flow of fluid from line 24. This results in a significant savings in irrigation fluid and also alleviates the mess and discomfort usually associated with prior known instruments.

Because piston 40 slides over the inner end 13 of sheath 12 and spring 52 is encapsulated between the OD of the sheath and the ID of barrel 16, no resected tissue, blood clots, etc. can get caught up in the coils of the spring, since there is a clear flow path rearwardly through the bores of sheath 12 and piston 40 to rear end 17 of barrel 16.

While a particular valve assembly 30 has been illustrated in the drawings, other designs and constructions may be utilized to open and close fluid flow from the irrigation line 24 in response to insertion and removal of the various surgical tools from the sheath assembly 12. Thus, the claims which follow are not limited to the specific construction of the valve assembly illustrated in the drawings and described herein above.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all change which come within the meaning and range of equivalency of the claims are therefore intended to be embraced therein.

What is claimed is:

1. A medical instrument comprising:
    a sheath assembly including:
        an elongated tubular sheath having an outer end adapted to be inserted into the body of a patient and an inner end;
        a barrel connected to said inner end of said tubular sheath and having a cylindrical bore aligned on the longitudinal axis of said tubular sheath, said barrel having a passageway through which irrigation fluid in introduced into said cylindrical bore; and
    a medical tool axially insertable into and removable from said barrel and said tubular sheath of said sheath assembly; and
    valve means associated with said barrel of said sheath assembly for automatically opening and closing said passageway in response to actuation by said medical tool as said medical tool is inserted into and removed from said barrel and said sheath, whereby fluid flow through said passageway is stopped automatically as said medical tool is removed from said sheath and said barrel.

2. The medical instrument of claim 1, said barrel having a radial opening forming part of said fluid passageway, said valve means including a cylindrical piston mounted within said bore of said barrel for axial movement between a first position in which it prevents fluid flow through said radial opening and a second position in which it permits fluid flow through said radial opening.

3. The medical instrument of claim 2, comprising spring means for urging said piston toward said first position.

4. The medical instrument of claim 3, wherein said piston includes an axial bore and said tool is insertable axially through said piston bore and said sheath and is engageable against said piston to move said piston axially from said first position to said second position.

5. The medical instrument of claim 3, wherein said piston includes an axial bore and said inner end of said tubular sheath extends axially within said piston bore, said spring means being a coil spring surrounding the outside of said inner end of said tubular sheath.

6. The medical instrument of claim 5, wherein said tool in insertable axially through said piston and said sheath and is engageable against said piston to move said piston axially from said first position to said second position.

7. A medical sheath assembly including a tubular sheath having an outer end adapted to be inserted into the body of a patient and an inner end;
    a barrel connected to said inner end of said tubular sheath and having a cylindrical bore aligned on the longitudinal axis of said tubular sheath, said barrel having a passageway through which irrigation fluid is introduced into said cylindrical bore; and
    valve means associated with said barrel and movable between a normally closed position and an open position for automatically opening and closing said passageway in response to axial insertion and removal of a medical tool from said barrel and said tubular sheath, said valve means being positioned in said normally closed position so that no fluid flows through said passageway when the medical tool is absent from said barrel and said sheath.

8. The medical sheath assembly of claim 7, said barrel having a radial opening forming part of said fluid passageway, said valve means including a cylindrical piston mounted within said cylindrical bore for axial movement between a first position in which it prevents fluid flow through said radial opening and a second position in which it permits fluid flow through said radial opening.

9. The medical sheath assembly of claim 8, comprising spring means for urging said piston toward said first position.

10. The medical sheath assembly of claim 9, wherein said piston includes an axial bore and said inner end of said tubular sheath extends axially within said piston bore, said spring means being a coil spring surrounding the outside of said inner end of said tubular sheath.

11. A medical instrument comprising:
a tubular device having:
a barrel section;
an elongated tubular sheath section extending outwardly from said barrel section and adapted to be inserted into the body of a patient; and
a bore extending axially through said barrel section and said sheath section, said barrel section having a passageway through which irrigation fluid is introduced into said bore; and
a medical tool axially insertable into and removable from said bore of said tubular device; and
valve means associated with said barrel section of said tubular device for automatically opening and closing said passageway in response to actuation by said medical tool as said medical tool is axially inserted and removed from said bore, whereby fluid flow through said passageway is stopped automatically as said tool is removed from said bore.

12. The medical instrument of claim 11, said barrel section having a radial opening forming part of said fluid passageway, said valve means including a cylindrical piston mounted within said barrel section for axial movement between a first position in which it prevents fluid flow through said radial opening and a second position in which it permits fluid flow through said radial opening.

13. The medical instrument of claim 12, comprising spring means for urging said piston toward said first position.

14. The medical instrument of claim 13, wherein said piston includes an axial bore and said tool is insertable axially through said piston bore and said sheath section and is engageable against said piston to move said piston axially from said first position to said second position.

15. A medical sheath device comprising:
a barrel section;
an elongated tubular sheath section extending outwardly from said barrel section and adapted to be inserted into the body of a patient;
a bore extending axially through said barrel section and said sheath section, said barrel section having a passageway through which irrigation fluid is introduced into said bore; and
valve means associated with said barrel section and movable between a normally closed position and an open position for automatically opening and closing said passageway in response to axial insertion and removal of a medical tool from said bore, said valve means being positioned in said normally closed position so that no fluid flows through said passageway when the medical tool is absent from said bore.

16. The device of claim 15, said barrel section having a radial opening forming part of said fluid passageway, said valve means including a cylindrical piston mounted within said barrel section for axial movement between a first position in which it prevents fluid flow through said radial opening and a second position in which it permits fluid flow through said radial opening.

17. The device of claim 16, comprising spring means for urging said piston toward said first position.

* * * * *